US00PP11370P

United States Patent [19]

Kientzler

[11] Patent Number: Plant 11,370

[45] Date of Patent: May 2, 2000

[54] NEW GUINEA IMPATIENS PLANT NAMED 'KICARL'

[75] Inventor: Ludwig Kientzler, Gensingen, Germany

[73] Assignee: Paul Ecke Ranch, Inc., Encinitas, Calif.

[21] Appl. No.: 09/127,641

[22] Filed: Jul. 31, 1998

[51] Int. Cl.[7] ..... A01H 5/00

[52] U.S. Cl. ..... Plt./318

[58] Field of Search ..... Plt./318

[56] References Cited

U.S. PATENT DOCUMENTS

P.P. 8,457 11/1993 Kientzler ..... Plt./318

P.P. 9,236 8/1995 Dehan ..... Plt./318

P.P. 10,300 3/1998 Cosner et al. ..... Plt./318

P.P. 11,022 8/1999 Bull ..... Plt./318

*Primary Examiner*—Howard J. Locker

*Assistant Examiner*—Kent L. Bell

*Attorney, Agent, or Firm*—C. A. Whealy

[57] ABSTRACT

A new and distinct cultivar of New Guinea Impatiens plant named 'Kicarl', characterized by its numerous reddish purple-colored flowers; upright and somewhat spreading growth habit; very freely branching, dense and bushy plant haibt; and dark green leaves with dark purple-red lower surfaces.

1 Drawing Sheet

BACKGROUND OF THE INVENTION

The present invention relates to a new and distinct cultivar of New Guinea Impatiens plant, botanically known as *Impatiens hawkeri*, and hereinafter referred to by the cultivar name 'Kicarl'.

The new cultivar is a product of a planned breeding program conducted by the Inventor in Gensingen, Germany. The objective of the breeding program was to develop early-flowering varieties with numerous flowers, uniform plant habit, attractive flower and foliage colors, and good flower form.

The new cultivar originated from a cross made by the Inventor of the proprietary selection identified as MF 329 as the male, or pollen parent, with the cultivar 'Aruba' (disclosed in U.S. Plant Pat. No. 8,456) as the female, or seed parent.

The cultivar 'Kicarl' was discovered and selected by the Inventor as a flowering plant within the progeny of the stated cross in a controlled environment in Gensingen, Germany, in April, 1996.

Asexual reproduction of the new cultivar by terminal cuttings taken at Gensingen, Germany, has shown that the unique features of this new Impatiens are stable and reproduced true to type in successive generations of asexual reproduction.

SUMMARY OF THE INVENTION

The following traits have been repeatedly observed and are determined to be the unique characteristics of 'Kicarl'. These characteristics in combination distinguish 'Kicarl' as a new and distinct cultivar:

1. Numerous red purple-colored flowers.
2. Upright and somewhat spreading growth habit.
3. Very freely branching, dense and bushy plant habit.
4. Very dark green leaves with dark purple-red lower surfaces.

Plants of the new New Guinea Impatiens are larger and have larger flowers than plants of the male parent, the proprietary selection identified as MF 329. In addition, plants of the new New Guinea Impatiens differ from plants of the proprietary selection MF 329 in leaf color.

Plants of the new New Guinea Impatiens are similar in flower color to plants of the female parent, the cultivar 'Aruba'. However, in side-by-side comparisons conducted in Encinitas, Calif., plants of the new New Guinea Impatiens differ from plants of the cultivar 'Aruba' in the following characteristics:

1. Plants of the new New Guinea Impatiens are more upright and open with longer internodes than plants of the cultivar 'Aruba'.
2. Plants of the new New Guinea Impatiens have longer and narrower leaves than plants of the cultivar 'Aruba'.
3. Flowers of plants of the new New Guinea Impatiens are brighter red purple than plants of the cultivar 'Aruba'.
4. Plants of the new New Guinea Impatiens have more rounded and slightly larger flowers than plants of the cultivar 'Aruba'.
5. Plants of the new New Guinea Impatiens flowered about 7 to 10 days earlier than plants of the cultivar 'Aruba'.

A detailed comparison of plants of the cultivars 'Kicarl' and 'Aruba' appears in Chart A at the end of the specification.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a top perspective view of a typical plant of the cultivar 'Kicarl'.

The photograph at the bottom of the sheet comprises a comparison close-up view of typical flowers and leaves of the cultivars 'Kicarl' (left) and 'Aruba' (right). Flower and foliage colors in the photographs may differ from the actual colors due to light reflectance.

DETAILED BOTANICAL DESCRIPTION

Plants of the cultivar 'Kicarl' have not been observed under all possible environmental conditions. The phenotype may vary somewhat with variations in environment such as temperature and light intensity, without, however, any variance in genotype. The following observations, measurements and comparisons describe three plants measured separately in 25-cm hanging baskets in Encinitas, Calif., under commercial practice in a polyethylene-covered greenhouse with day temperatures ranging from 21 to 32° C. and night temperatures ranging from 16 to 18° C. and light levels of about 3,500 footcandles.

In the following description, color references are made to The Royal Horticultural Society Colour Chart except where general terms of ordinary dictionary significance are used.

Classification:

*Botanical.*—*Impatiens hawkeri* cultivar 'Kicarl'.

*Commercial.*—New Guinea Impatiens cultivar 'Kicarl'.

Parentage:

*Male parent.*—Proprietary selection of *Impatiens hawkeri* identified as MF 329.

*Female parent.*—*Impatiens hawkeri* cultivar 'Aruba', disclosed in U.S. Plant Pat. No. 8,456.

Propagation:

*Type cutting.*—Terminal cuttings.

*Time to initiate roots.*—Summer: About 14 days with 21° C. soil temperature. Winter: About 18 days with 21° C. soil temperature.

*Time to develop roots.*—Summer: About 21 days with 21° C. soil temperature. Winter: About 24 days with 21° C. soil temperature.

Plant description:

*Plant form.*—Upright and somewhat spreading; "V"-shaped.

*Growth habit.*—Vigorous. Very freely branching, dense and bushy growth. Appropriate for 10 to 25-cm containers.

*Crop time.*—From planting of a rotted cutting, about six to eight weeks are required to produce a finished flowering plant in a 12.5-cm container.

*Plant size.*—Height: About 30 cm. Width or spread: About 35 cm.

*Lateral branches.*—Quantity: About 11. Length: About 24 cm. Diameter: About 7 mm. Internode length: About 5.75 cm. Color: 60A.

*Foliage description.*—Leaves simple, generally symmetrical, abundant, opposite or in whorls, horizontal to plant. Mostly flat. Length: About 10 cm. Width: About 3.4 cm. Shape: Elliptic with acuminate apex, attenuate base and crenate to serrulate margin with ciliation. Texture: Smooth, somewhat glossy. Color: Young foliage, upper surface: 147A. Young foliage, lower surface: 59A. Fully expanded foliage, upper surface: Darker than 147A. Fully expanded foliage, lower surface: 59B. Venation, upper surface: 59A. Venation, lower surface: 59A. Petiole: Length: About 5 cm. Diameter: About 2.5 mm. Color: 59C.

Flower description:

*Flower type and habit.*—Reddish purple-colored flowers. Freely and continuously flowering. Flowers arise from leaf axils. Usually about 14 flowers and flower buds per lateral branch. Flowers positioned above the foliage and face upward and outward. Flowers slightly cupped and nearly rounded. Flowers persistent.

*Flowering season.*—Year-round under greenhouse conditions. In the garden, flowering is continuous from spring until fall. Flowers typically last less than one week depending on environmental and cultural conditions.

*Flower size.*—Length: About 5.5 cm. Width: About 5.5 cm. Depth: About 1.25 cm.

*Flower buds.*—Length: About 1.7 cm. Diameter: About 9 mm. Shape: Ovoid. Color: 80A.

*Petals.*—Quantity: Five. Length: Upper petal: About 2.6 cm. Middle petals: About 2.8 cm. Lower petals: About 3.4 cm. Width: Upper petal: About 4.2 cm. Middle petals: About 3 cm. Lower petals: About 3.2 cm. Shape: Cordate with acute base and entire margin. Texture: Velvety, slightly iridescent, smooth. Color: When opening, upper surface: Slightly more lavender than 74B; 44A at base. When opening, lower surface: 74B. Fully opened, upper surface: 74A/74B. Flower color does not fade; 44A at base. Fully opened, lower surface: 74B/74C.

*Spur.*—Length: About 6 cm. Shape: Narrow and curved. Color: 59B.

*Peduncles.*—Length: About 5.75 cm. Angle: Very acute. Strength: Strong. Color: 60B.

*Reproductive organs.*—Androecium: Stamen number: Five, anthers fused, filaments free. Anther shape: Obovate. Anther size: 3 mm by 5 mm. Anther color: 4D. Amount of pollen: Moderate. Pollen color: 4B. Gynoecium: Five-loculate fused. Pistil length: About 4 mm. Stigma color: 4D. Ovary color: 146A.

Disease resistance: Under commercial conditions, resistance to pathogens has not been observed.

Seed development: Seed production has not been observed.

CHART A

| CHARACTERISTIC | 'KICARL' | 'ARUBA' |
|---|---|---|
| GROWTH HABIT, PLANT SHAPE | Upright, somewhat spreading; "V"-shaped | Spreading, mounded |
| PLANT HEIGHT | About 30 cm | About 25 cm |
| STEM COLOR | 60A | 59A |
| INTERNODE LENGTH | About 5.75 cm | About 5.25 cm |
| LEAF LENGTH | About 10 cm | About 8.75 cm |
| LEAF WIDTH | About 3.4 cm | About 3.9 cm |
| LEAF COLOR, MATURE, LOWER SURFACE | 59B | 59A |
| PETIOLE LENGTH | About 5 cm | About 4 cm |
| FLOWER SHAPE | Nearly round | Rounded triangle |
| FLOWER DIAMETER | About 5.5 by 5.5 cm | About 4.5 by 5.5 cm |
| PEDUNCLE ANGLE | Very acute | Upward and outward |
| PEDUNCLE COLOR | 60B | 61C |

It is claimed:

1. A new and distinct cultivar of New Guinea Impatiens plant named 'Kicarl', as illustrated and described.

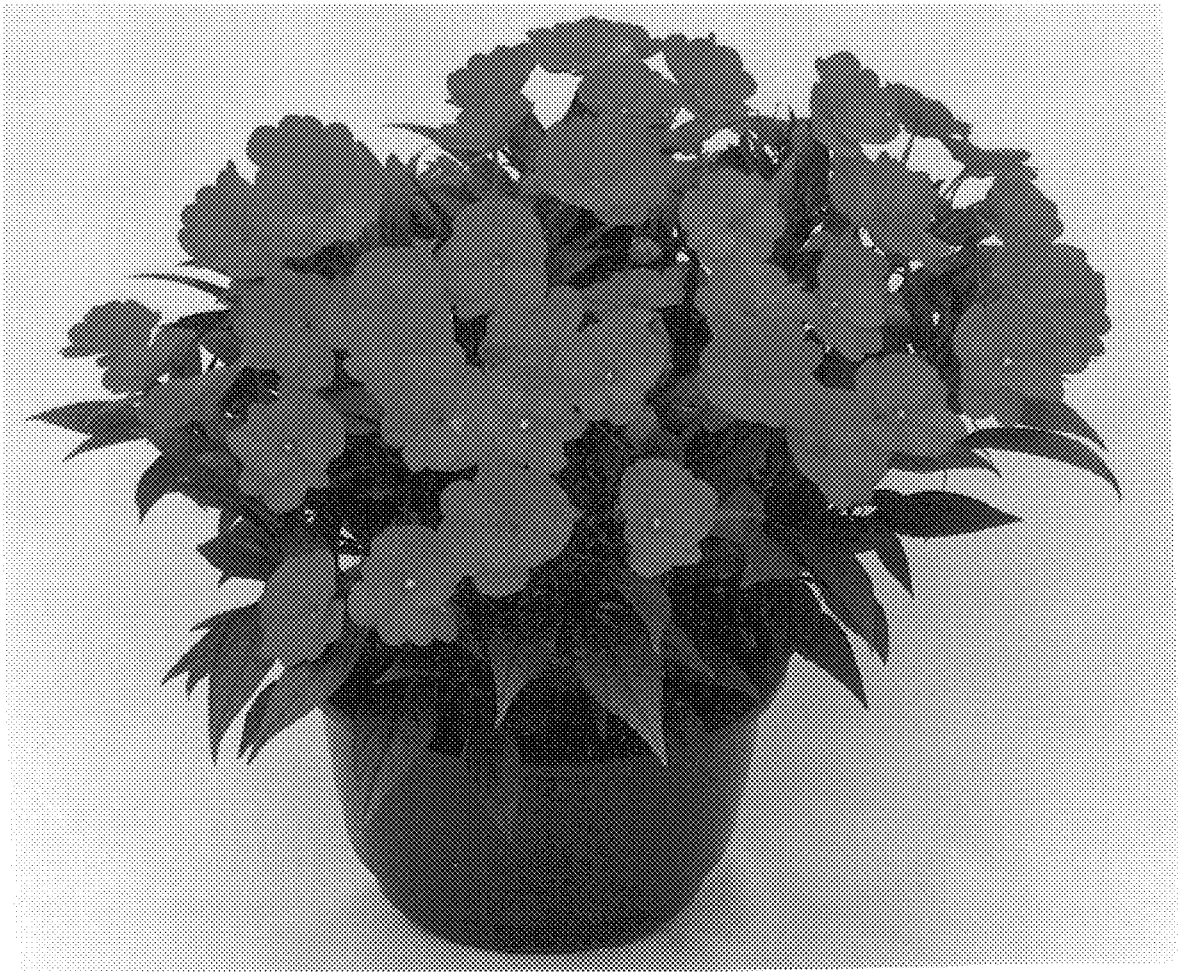
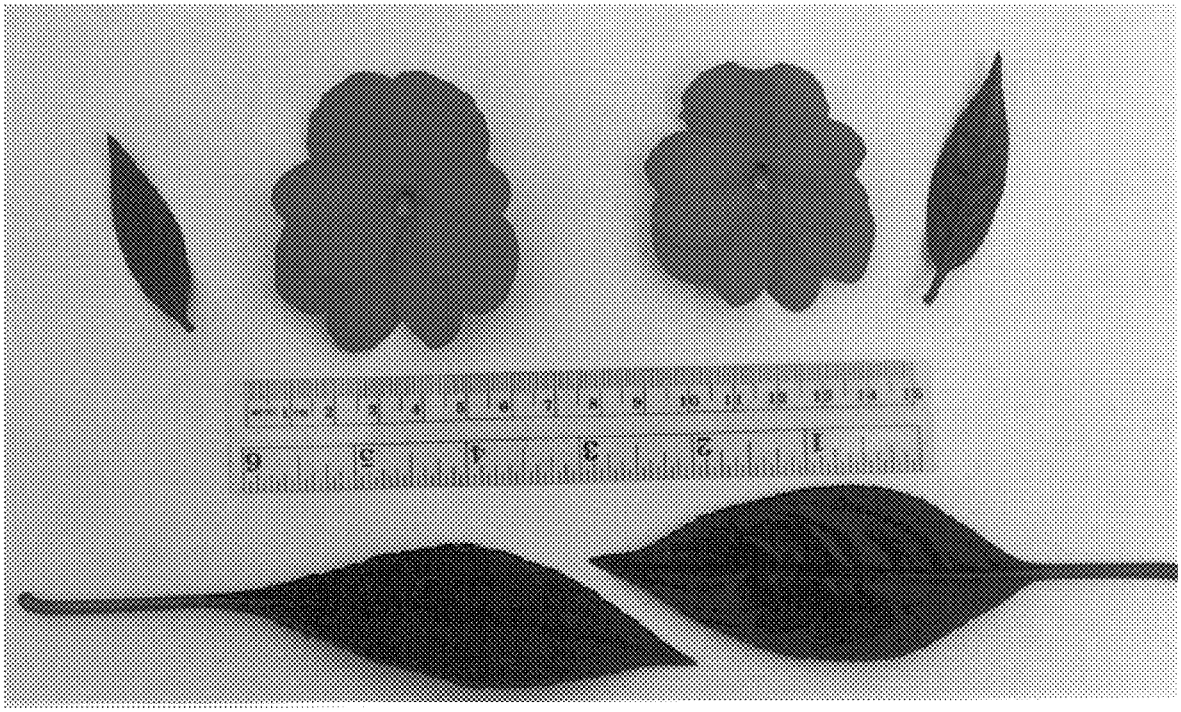

* * * * *